(12) United States Patent
Kapoor

(10) Patent No.: US 8,855,757 B2
(45) Date of Patent: Oct. 7, 2014

(54) MOBILE WELLNESS DEVICE

(71) Applicant: Rijuven Corporation, Pittsburgh, PA (US)

(72) Inventor: Rajeshwar Kapoor, Pittsburgh, PA (US)

( * ) Notice: Subject to any disclaimer, the term of this patent is extended or adjusted under 35 U.S.C. 154(b) by 0 days.

(21) Appl. No.: 13/694,594

(22) Filed: Dec. 14, 2012

(65) Prior Publication Data

US 2013/0158423 A1    Jun. 20, 2013

(51) Int. Cl.
*A61B 5/0432* (2006.01)
*A61B 7/02* (2006.01)
*A61B 5/024* (2006.01)
*A61B 5/0404* (2006.01)
*G06F 19/00* (2011.01)
*A61B 5/00* (2006.01)
*A61B 5/0408* (2006.01)

(52) U.S. Cl.
CPC ........... *A61B 5/0432* (2013.01); *G06F 19/3418* (2013.01); *A61B 5/0006* (2013.01); *A61B 5/6898* (2013.01); *A61B 7/02* (2013.01); *A61B 5/02405* (2013.01); *A61B 5/0404* (2013.01); *A61B 5/0408* (2013.01); *A61B 5/486* (2013.01); *A61B 5/6815* (2013.01); *A61B 2560/0412* (2013.01); *A61B 2562/227* (2013.01)
USPC ........................................................ 600/523

(58) Field of Classification Search
CPC . A61B 5/0006; A61B 5/0404; G06F 19/3418
USPC ........................................................ 600/523
See application file for complete search history.

(56) References Cited

U.S. PATENT DOCUMENTS

| 2004/0106875 A1* | 6/2004 | Menzie et al. | 600/509 |
| 2006/0025696 A1* | 2/2006 | Kurzweil et al. | 600/509 |
| 2007/0249946 A1* | 10/2007 | Kumar et al. | 600/515 |
| 2009/0082685 A1* | 3/2009 | Stabler et al. | 600/523 |

* cited by examiner

*Primary Examiner* — Michael Kahelin

(57) ABSTRACT

The invention is directed to a system for acquiring electrical footprint of the heart, electrocardiogram (EKG or ECG) and heart rate variability monitoring, incorporated into a mobile device accessory. The ECG signal is conveniently acquired and transmitted to a server via the mobile device, offering accurate heart rate variability biofeedback measurement which is portable and comfortable during normal daily life. The invention provides a reliable tool for applications such as wellness, meditation, relaxation, sports and fitness training, and stress-relief therapy where accurate heart rate variability measurement is desired.

19 Claims, 10 Drawing Sheets

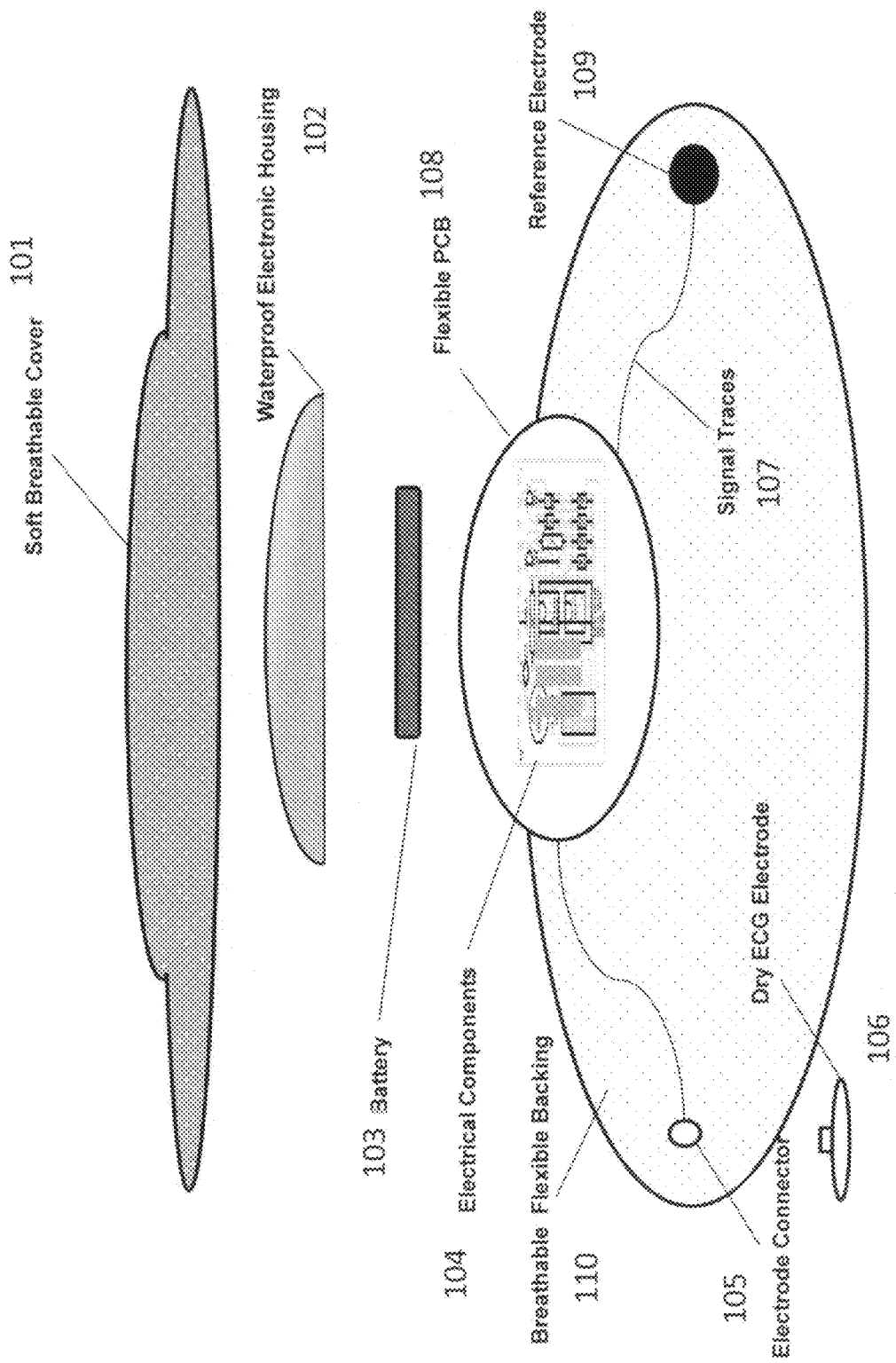

MOBILE WELLNESS DEVICE

REFERENCE TO CO-PENDING APPLICATION(S)

The present application is a continuation of U.S. Provisional Patent Application Ser. No. 61/630,555, filed on Dec. 14, 2011 which is related to U.S. Provisional Patent Application Ser. 61/629,318 filed on Nov. 16, 2011, the entire disclosures of which are hereby incorporated by reference.

TECHNICAL FIELD

The present invention relates to the field of portable devices and more particularly to portable devices comprising a biometric sensor arrangement for measuring one or more intrinsic physical or health characteristic of a human.

BACKGROUND OF THE INVENTION

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with various arrhythmias genesis, including ventricular tachycardia and atrial fibrillation.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Neural stimulation can be used to stimulate nerve traffic or inhibit nerve traffic. An example of neural stimulation to stimulate nerve traffic is a lower frequency signal (e.g. within a range on the order of 20 Hz to 50 Hz). An example of neural stimulation to inhibit nerve traffic is a higher frequency signal (e.g. within a range on the order of 120 Hz to 150 Hz). Other methods for stimulating and inhibiting nerve traffic have been proposed. According to various embodiments of the present subject matter, sympathetic neural targets include, but are not limited to, a peroneal nerve, a sympathetic column in a spinal cord, and cardiac post-ganglionic sympathetic neurons. According to various embodiments of the present subject matter, parasympathetic neural targets include, but are not limited to, a vagus nerve, a baroreceptor, and a cardiac fat pad. Neural stimulation can be selectively delivered to afferent neural pathways, selectively delivered to efferent neural pathways, or delivered to both afferent and efferent neural pathways. For example, some embodiments selectively stimulate or inhibit only parasympathetic afferents or only parasympathetic efferents, and some embodiments selectively stimulate or inhibit sympathetic afferents or efferents.

The present subject matter can be used to prophylactically or therapeutically treat various diseases by modulating autonomic tone. Examples of such diseases or conditions include hypertension, cardiac remodeling, and heart failure.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the FrankStarling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction (decompensation). It has been shown that the extent of ventricular remodeling is positively correlated with increased mortality in post-MI and heart failure patients.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

The prior art teaches many way of measuring heart rate. A stethoscope is traditionally used to amplify these sounds and present them to a caregiver. The acoustic principle may also be used in other ways, both manual and automated, at various parts of the body. Another way is the pulse oximeter approach. In pulse oximeters, a light of a known frequency through an area of the body, such as the fingertip or earlobe, and detect the same light once it has either passed through the body or been reflected back to a photo sensor. With each heart beat, oxygen-rich blood is momentarily pushed through the capillaries in that region. This momentary increase in the oxygen content of the blood upon each heart beat changes the optical properties of the blood. As the light passes through the fingertip or earlobe, specific frequencies are absorbed to varying degrees, depending on the amount of oxygen in the blood, and are therefore not present in the returning light. The change in detected frequencies occurring once per heart beat allows for detection of individual heart beats, and thus a heart rate measurement. The degree of spectral change is used to determine the oxygen content in the blood. Another measurement method makes use of the varying outward pressure applied against the skin by major arteries. With each heart beat, a surge of blood passes through the arteries. In an artery of sufficient size, and located near to the surface of the body, this momentary pressure can be detected by holding a pressure sensor, such as a piezo-electric (P-E) element, in place over the artery location. The P-E element is physically stretched by the momentary outward pressure of the artery during a heart-beat. As it is stretched, the altered shape of the P-E element changes its electrical characteristics—e.g., a change in its resistance to a current passing through it. Changes in the resistance of the P-E are then detected by appropriate circuitry, and used to identify heart beats and thus heart rate. Suitable surface arteries and sensing devices are well known in the art and include sensing at the wearer's wrist, the temple, the inner ear, or the bridge of the nose.

Heart rate monitoring using the chest strap method has become increasingly popular for sports and fitness training as well as for some other activities such as relaxation training, stress relief and meditation in which heart rate as a biofeedback item has been found useful. During this time, the chest strap has remained in much the same form, as a practical means of obtaining a continuous, accurate heart rate reading for these largely non-medical purposes. However, for many users, the chest strap may chafe causing discomfort. Many users find them awkward to put on, uncomfortable to wear, and bothersome to keep handy. In addition, they can be restrictive of good chest expansion and thus restrict full breathing during exercise. For wearers with slender ribs and torsos, the chest strap can slip down out of the proper position and cease to function properly. Stretched across the chest, they are perceived by some as unmanly, or unwomanly, or as interfering with tan lines or undergarments.

There are various physiological factors affecting the autonomic regulation of heart rate: respiration, thermoregulation, hormonal regulation, blood pressure, cardiac output, etc. One of the most important factors is blood pressure. There are special cells in the heart and large blood vessels that sense blood pressure level and send afferent stimulation to the central structures of the ANS that control HR and blood vessel tonus forming a continuous feedback to maintain an optimal level of the blood pressure.

This mechanism is also called baroreflex. It increases HR when blood pressure drops and vice versa and thus maintains a short-term stable blood supply to the vital organs.

One of the best ways to assess the autonomic function is to analyze minute changes in heart rate, which are caused by many factors including regulatory influence of the autonomic nervous system.

A special method of analysis can be applied to recorded heart rate readings. It is called Heart Rate Variability (HRV) analysis. The HRV analysis is a powerful, very accurate, reliable, reproducible, yet simple to do.

It is found that lowered HRV is associated with aging, decreased autonomic activity, hormonal tonus, specific types of autonomic neuropathies (e.g. diabetic neuropathy) and increased risk of sudden cardiac death after acute heart attack.

Other research indicated that depression, panic disorders and anxiety have negative impact on autonomic function, typically causing depletion of the parasympathetic tonus. On the other hand an increased sympathetic tonus is associated with lowered threshold of ventricular fibrillation. These two factors could explain why such autonomic imbalance caused by significant mental and emotional stress increases risk of heart attack followed by sudden cardiac death.

Aside from that, there are multiple studies indicating that HRV is quite useful as a way to quantitatively measure physiological changes caused by various interventions both pharmacological and non-pharmacological during treatment of many pathological conditions having significant manifestation of lowered HRV.

However it is important to realize that clinical implication of HRV analysis has been clearly recognized as a predictor of risk of arrhythmic events or sudden cardiac death after acute heart attack, and as clinical marker of diabetic neuropathy evolution.

Nevertheless, as the number of clinical studies involving HRV in various clinical aspects and conditions grows, HRV remains one of the most promising methods of investigating general health in the future.

There is an ongoing need for an improved system and method for heart rate, heart rate variability, wellness and fitness monitoring that is user friendly and less invasive.

SUMMARY OF THE INVENTION

One object of the invention is to provide a mobile system that monitors the electrical conductivity of the heart for heart rate variability analysis that tracks health changes and be aware of possible health issues on its early stage, wherein a user can track health changes and reveal health trends, react quickly on detected health issues and to help improve overall health and wellness.

A second aspect of the of the invention is to provide a mobile system that monitors the electrical conductivity of the heart for heart rate variability analysis that can determine a person's biological age and optimize anti-aging procedures, wherein a user can track biological age changes over time, get alerted about sudden changes in biological age and ultimately improve life quality and get younger.

A third aspect of the invention is to provide a mobile system that monitors the electrical conductivity of the heart for heart rate variability analysis that assesses current fitness level and measure daily fitness progress, wherein a user can track fitness progress over time, review fitness level on a worldwide scale and compared to other people within a particular age and gender group.

A fourth aspect of the invention is to provide a mobile system that monitors the electrical conductivity of the heart for heart rate variability analysis to monitor and manage stress, build a strong stress-resistance, wherein stress is reduced with biofeedback control, the body is trained to withstand stress attack, and to help normalized blood pressure.

DETAILED DESCRIPTION

Brief Description of the Drawings

The present invention will now be described in more detail with reference to the enclosed drawings, in which:

FIG. 10 shows a version of the ECG recorder in the form of a chest patch.

DETAILED DESCRIPTION

Figure 1:
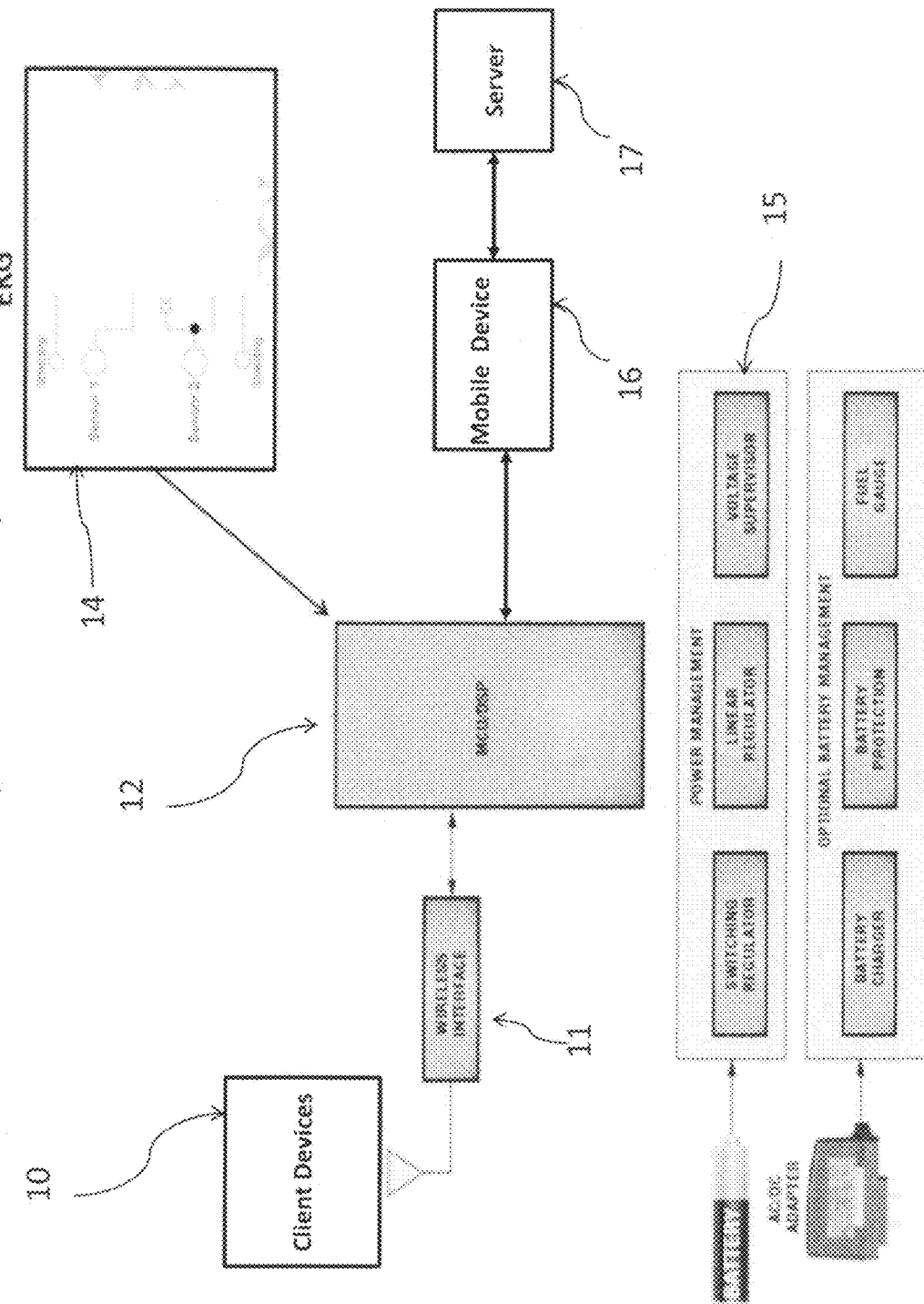
FIG. 1 shows a block diagram of the overall system comprising of a mobile ECG system a mobile device and backend server.

The inventive system, in accordance to FIG. 1, consists of an electrical footprint of the heart or ECG recorder device. The ECG recorder device consists of a microprocessor 12, power management 15, dry ECG sensors and processor 14. The ECG recorder includes wireless interface 11 capable of communicating with client devices 10 such as a mobile device 16. The mobile device includes software component running on it, interfacing the ECG recorder with a back-end server 17, with the capability to capture and save ECG data, and analyzes it to obtain a marker for heart rate variability.

In a preferred embodiment, the ECG recorder interfaces with the mobile or cellular phone via Bluetooth wireless communication protocol to mobile device 16. The ECG recorder can also connect with the mobile device 16 via wireless local area network (WLAN) products that are based on the Institute of Electrical and Electronics Engineers' (IEEE) 802.11 standards such as Wi-Fi.

Customized software application is installed on the mobile device 16 to review physiologic data of a patient and to (a) view the near real-time waveforms remotely (b) remotely review other standard patient data. The customized software can display at least the following physiologic information: ECG Waveform, health assessment metrics such as Overall Health and Wellness, Biological clock, Fitness Level and Stress Level.

The CPU processor 12 comprises a tangible medium, for example read only memory (ROM), electrically erasable programmable read only memory (EEPROM) and/or random access memory (RAM). The processor 12 may also be comprised many known real time clock and frequency generator circuitries, for example the PIC series of processors available from Microchip, of Chandler Ariz. In some embodiments, processor may comprise the frequency generator and real time clock.

Figure 2:
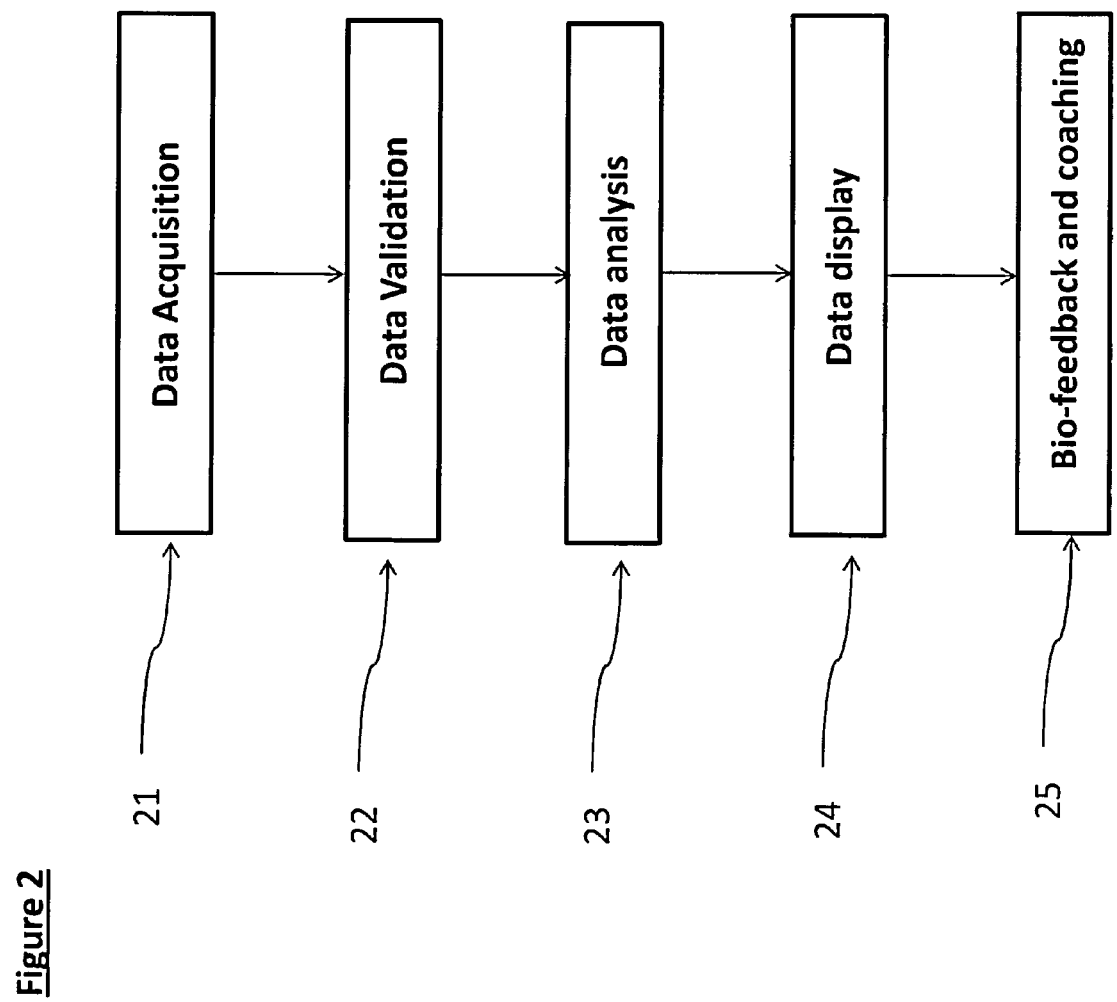
FIG. 2 shows a flow diagram of the mobile ECG system.

In FIG. 2, the ECG recorder acquires heart electrical footprint or ECG data from the user 21. The ECG data gets sent to the mobile device 16, where it gets validated 22. The mobile device sends the ECG data to the backend server for further analysis 23. After analysis, the backend server sends the health module information to the mobile 16 where it gets displayed 24 for biofeedback and coaching 25.

Figure 3:
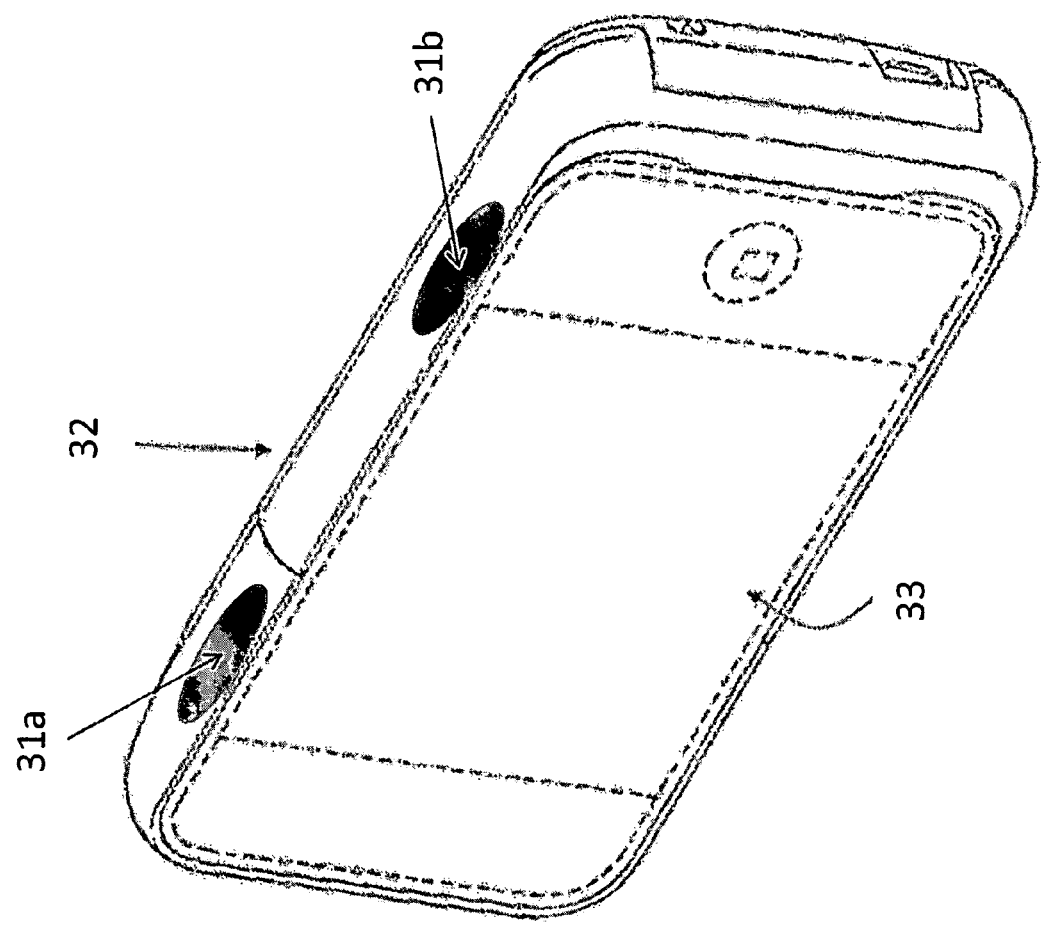
FIG. 3 shows an ECG recorder in the form of a mobile case.

FIG. 3 shows an exemplary ECG recorder in the form of a mobile cover case 32 (also referred to as "cover"). The cover 32 can also be a mechanism that partially covers the mobile device 33. The cover 32 encompasses at least two electrodes 31a-b, on its sides or back to establish contact with the user's fingers and/or chest. The electrodes can be made out of stainless steel, silicon nitride and silver-silver chloride, with dimensions between approximately 4 mm to about 10 mm in diameter or in width and height. The two electrodes 31a-b (positive and negative) may be paired with a third electrode to serve as a reference voltage (ground) for the differential amplifier and to improve common mode noise rejection.

Holding the cover in one hand, e.g., the left hand, the patient makes contact with one electrode, one on one side of the cover which contacts the thumb. The patient then touches the other side of the cover with the other hand, making contact with the other electrode to the other side. ECG and heart rate are thereby recorded for 1 to 5 minutes.

Figure 4:
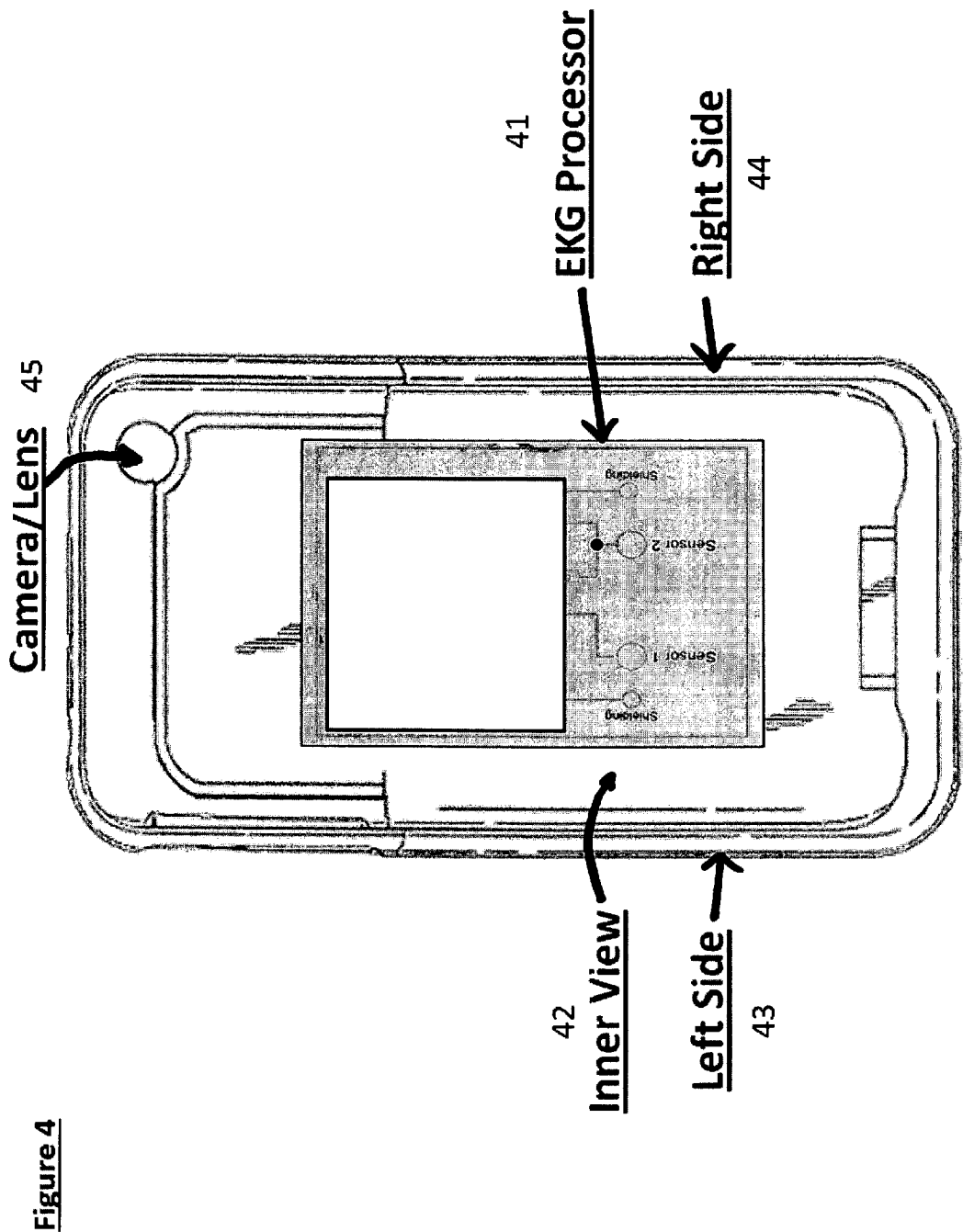
FIG. 4 shows another view of the ECG recorder in the form of a mobile case.

In FIG. 4, the cover contains electrodes are attached to a microprocessor 41 (MCU), performing bio-signal detection and processing. The MCU 41 is designed with advanced analog front end circuitry and a flexible, powerful digital signal processing structure. It targets bio-signal inputs ranging from uV to mV level and deployed with proprietary algorithms. The Low-Noise-Amplifier and ADC are the main components of the MCU 41 analog front end. It can detect bio-signals and convert them into digital words using a 16-bit high resolution analog digital converter (ADC). The heart of the MCU 41 digital circuit is a powerful system management unit. It is in charge of overall system configuration, operation management, internal/external communication, proprietary algorithm computation, and power management. The MCU 41 also comes with hardwired DSP blocks to accelerate calculations, such as various digital filtering, under the supervision of the system management unit. In other embodiments, the cover 33 is used as a Mobile Heart Rate Monitor for regular and long term usage for applications such as heart rhythm irregularity detection.

Figure 5:
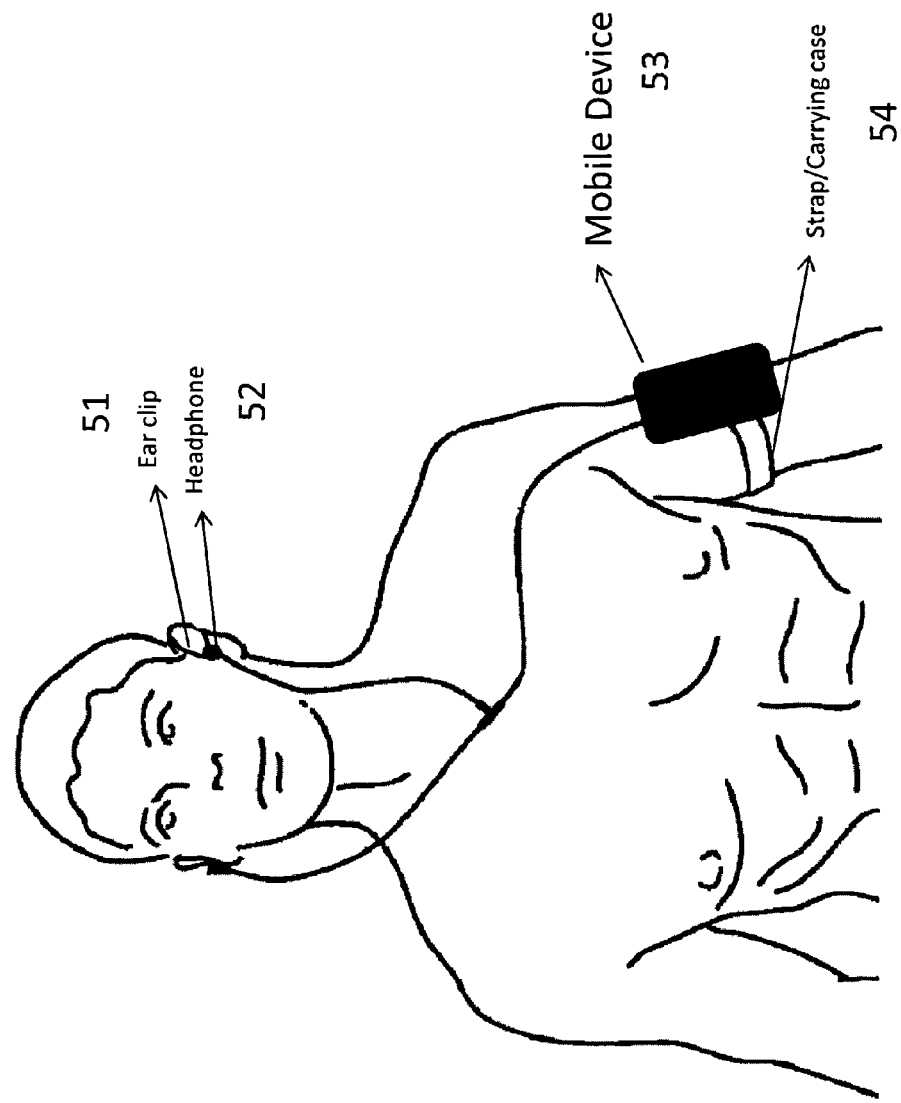
FIG. 5 shows an ECG recorder in the form of headphone and upper arm band.

According to one aspect shown in FIG. 5, the invention can be realized as a specially designed headphone 51, 52 and left extremity strap 54. The invention encompasses at least two electrodes on the inner or outer right ear (hereafter referred to as ear) and another on the left extremity. The electrodes are made out of stainless steel, silicon nitride or silver-silver chloride, with dimensions between approximately 3 mm to 10 mm in diameter or in width/length. The two electrodes in FIG. 7, 71a and b (positive and negative) are paired with a third electrode to serve as a reference voltage (ground) for the differential amplifier and to improve common mode noise rejection. The preferred system features a negative electrode on the right ear and a positive or ground electrode on a strap FIG. 6, 61, touching the skin on the lower arm.

Figure 8:
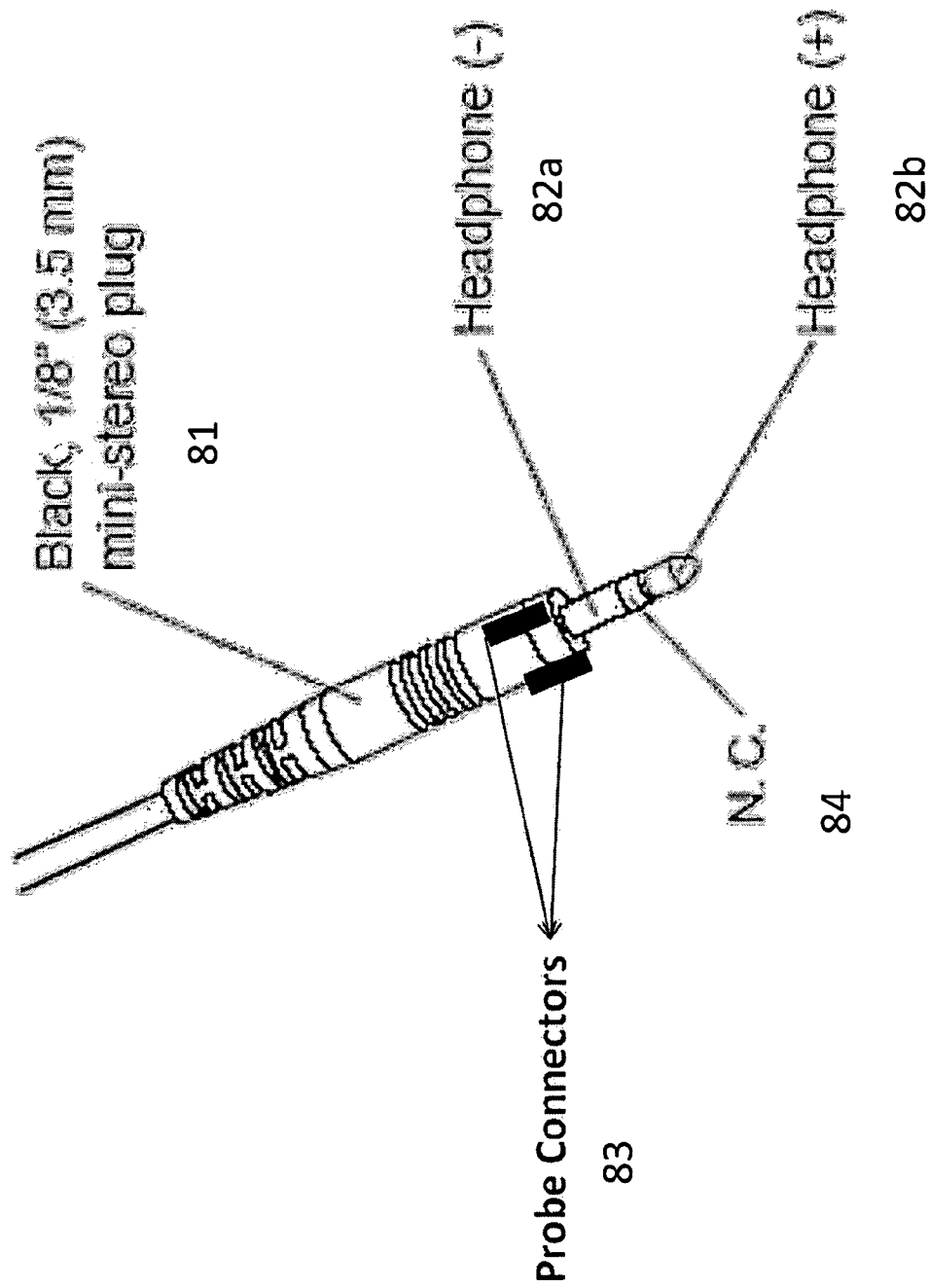
FIG. 8 shows a shows a headphone jack that works in conjunction with the headphone.

According to FIG. 8, wires connect these electrodes are mated with the main ECG recorder device via a specialized headphone jack. The Jack includes a mini stereo plug 81. The jack also includes electrical connectors 84, making connection with the main recorder device, which has circuitry capable of measuring the electrical voltage potential between the electrodes and to detect patterns therein corresponding to individual heart-beats and heart rate variability. EKG, heart rate and heart rate variability are thereby recorded for 1 to 5 minutes, and are reported to the user in various ways.

Figure 7:
FIG. 7 shows a version of the ECG recorder in the form of a headphone.

In another embodiment, the system has two electrodes FIG. 7, 71a-b, at least one electrode positioned to be in contact with the skin of the head, including the ear via a headphone or headset, and a second electrode positioned to be in contact either with the skin of the arm at the bicep (FIG. 5) or wrist, or else with the skin of the torso at the waist. The system serves as a headphone for listening to audio from an audio source device such as a portable MP3 player, a radio, a mobile telephone (e.g., cellular, portable, satellite, etc.), etc. An in-the-ear style of headphones, commonly known as "ear-buds", can be used. Ear-buds are commonly worn one bud in each ear, such that the outer surface of each bud enclosure is in contact with the skin of the folds of the ear. In this embodiment, the outer surface of the bud enclosure is modified to be electrically conductive and made to serve as an electrode connected to the heart-beat detection circuitry. Some ear-bud designs, which are popular among exercisers, also contain a structure designed to fit around the ear, thus holding the ear-bud in place during vigorous physical activity. Such a design may also, in this embodiment, provide contact surfaces around the ear which may be used to hold a conductive surface (electrode) in constant contact with the skin around the ear.

Figure 6:
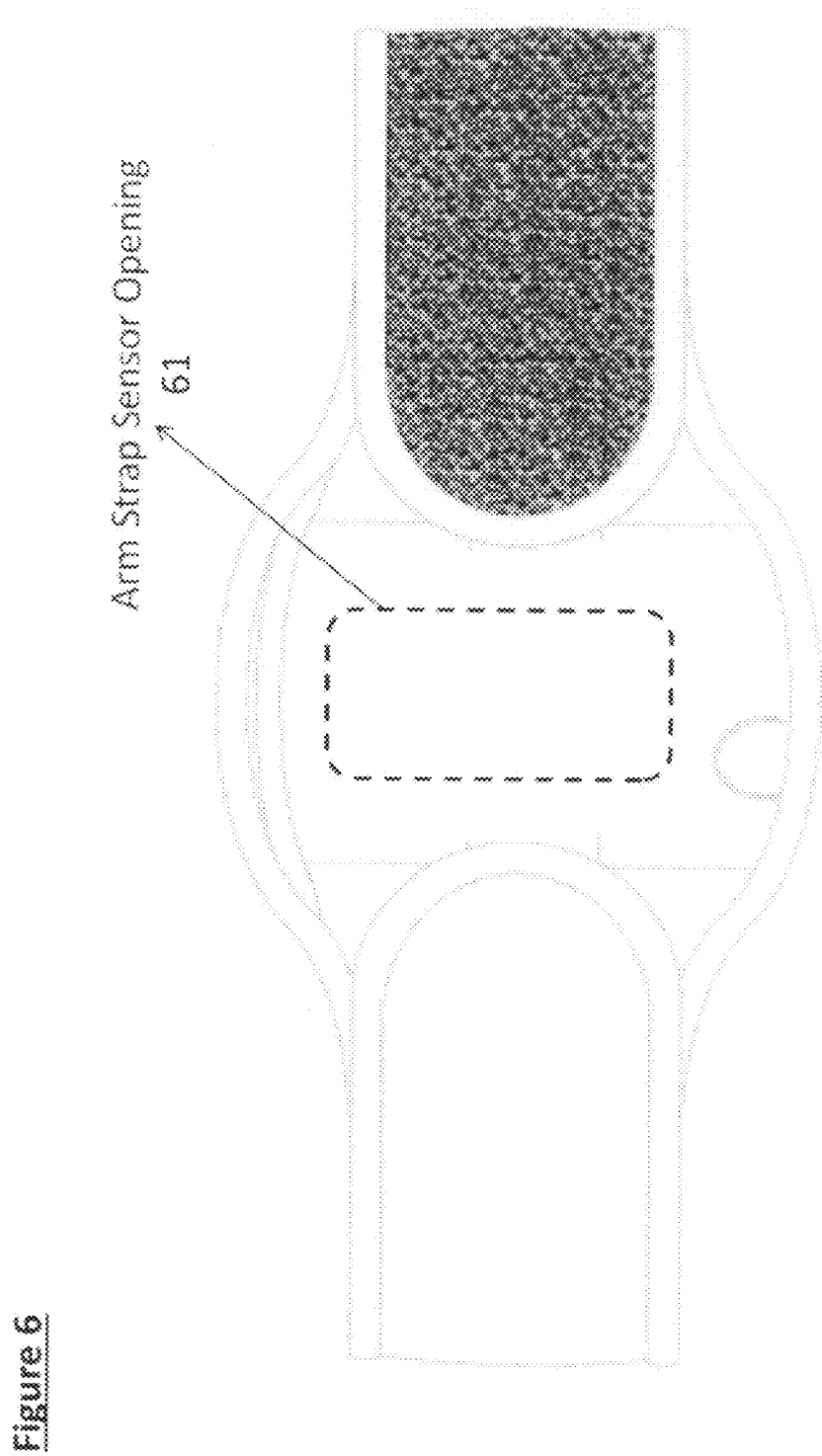
FIG. 6 shows an Arm Strap/band with sensor opening.

The other electrode can be integrated into a carrying case used for carrying portable audio devices FIG. 6, 54. Exercisers who wish to wear a portable audio device (MP3 player, radio, mobile telephone, etc.) frequently wear the audio source device in one of several locations: strapped to the upper arm, strapped to the wrist or forearm, clipped to the waistband of exercise clothing, held in the hand, etc. Features and aspects hereof may include an apparatus which holds the portable audio source device and the heart rate detection circuit in one of those convenient locations and integrates a conductive surface at that location to serve as one of the required electrodes connected to the heart rate detection circuit.

Figure 9:
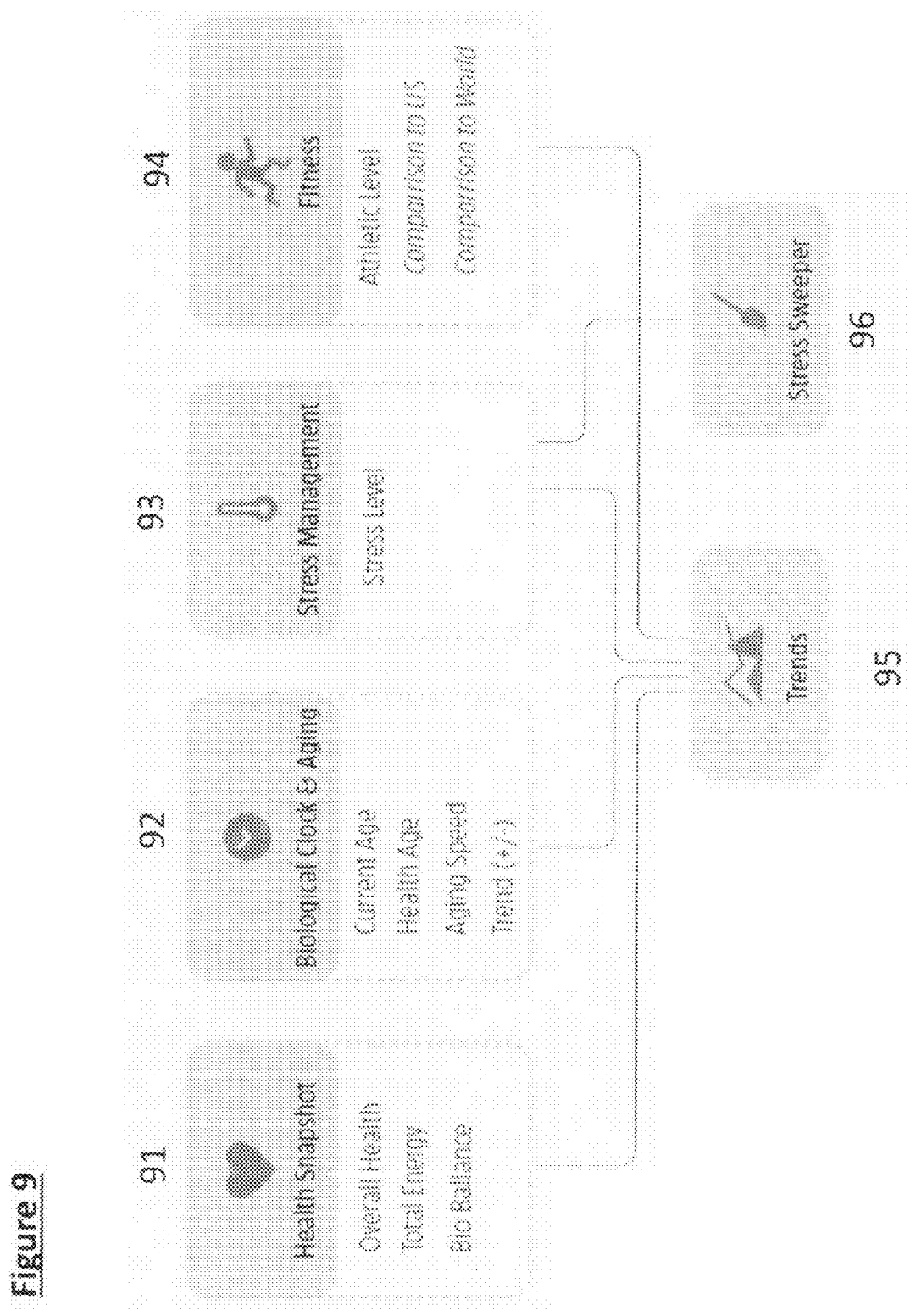
FIG. 9 shows exemplary health information modules that are being communicated to the user as a result of heart rate variability analysis.

HRV is being used to derive health assessment metrics, FIG. 9 such as overall health and wellness 91, aging 92, fitness 94 and stress 93. The source information for HRV analysis is continuous beat-by-beat (not averaged) recording of heartbeat intervals. The electrical footprint of the heart or Electrocardiograph (ECG or EKG) is considered as the best way to measure heartbeat intervals. ECG is an electrical signal reflecting minute changes in the electrical field generated by heart muscle cells. It is measured by a special electronic device with conductive electrodes placed on chest around heart area or limbs. ECG signal has a very specific and robust waveform simple to detect and analyze. Cardiac rhythm (sequence of heartbeat intervals) derived from ECG is the best way to detect normal heartbeats as well as all sorts of ectopic heartbeats, which must be excluded from the HRV analysis.

The autonomic nervous system function can be evaluated with the Autonomic Balance Test. This test is based on the short-term HRV analysis of resting heart rate recordings of 1 to 5 minutes long. Such recordings are assumed to be done at a steady-state physiological condition and should be properly standardized to produce comparable results.

According to the standards set forth by the Task Force of the European Society of Cardiology and North American Society of Pacing and Electrophysiology in 1996, there are two methods of analysis of HRV data: time- and frequency-domain analysis. For both methods the heartbeat intervals should be properly calculated and any abnormal heartbeats found. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and vagus nerve activity.

The ECG recorder collects ECG data from users which gets analyzed and converted to HRV data the gives information about different states of the Autonomic Nervous System. It happens that ANS states vary from one individual to another, especially of different age and gender. The backend server 17 matches the state of the user's Autonomic Nervous System to the range of "healthy" states of individuals of within the age range and gender. The correct results about your health 91 and fitness 94 are determined.

Fitness assessment 94 is based on the one of the most accurate methods of fitness assessment. Analysis is done on ECG signal at the backend server that determines the autonomic nervous system's response on a simple standup maneuver. The standup maneuver causes heart rate to rise within the first 10-15 seconds because blood pressure drops due to gravitational redistribution of the blood mass. Then the cardiovascular system attempts to compensate an orthostatic effect of standing up by constricting peripheral blood vessels. As a result blood pressure returns to its normal level and heart rate drops. Athlete body reaction is fast and strong, while sedentary lifestyle makes body react with a delay and a little amplitude. This serves as a base of determining a fitness level.

This biological clock 92 is determined based on the body's ANS (autonomic nervous system) response on paced breathing. The risk of myocardial infarction and overall health condition of the body is evaluated.

The current invention makes an assessment of the autonomic nervous system regulatory function condition based Autonomic Balance—a ratio between levels of the sympathetic and parasympathetic activity and Autonomic Tonus—a net level of the sympathetic and parasympathetic activity.

There are three main types of the autonomic nervous system conditions: 1—Predominant parasympathetic nervous system function—typical for a state of relaxation, 2—Predominant sympathetic nervous system function—typical for a state of stress and 3—Balanced autonomic nervous system function—typical for an idle calm state.

Each of these three categories may have three different levels of the autonomic tonus: low, normal or high. The Autonomic Balance is calculated in points based on 80% of least deviated values of HRV parameters in the normative database. It ranges from −10 points to +10 points.

To make a conclusion on the HRV analysis, actual ECG readings of all HRV parameters are compared with their respective normal ranges specific to patient's age and gender. These normal ranges are taken from a normative database built in a special clinical study on a large pool of clinically validated healthy subjects.

Normal range is a range of values of certain HRV parameter representing statistical distribution of this parameter values in a large population of healthy individuals of selected age and gender. For instance, the logarithmic value of HF (ms^2/Hz) lies in range between 2.5 and 6.6 for males between 30 and 40 years old.

In this embodiment, a 48 years old male was tested with an autonomic balance test. The test results showed an HF parameter value of 3.1 on logarithmic scale of ms^2/Hz. A predicted value for 48 years old males is 4.03. One of the widely used approaches is determining a normal range based on criteria of statistical distribution of measured parameter values in healthy subjects. Typically normal range is considered within 95% of the interval of confidence in both directions. This range would fit 95% of all readings obtained from healthy subjects of the selected population. It is important to mention that there is a borderline zone (or conditional norm) in near proximity to the borders of the normal range. Actual readings falling into this zone have higher risk to be abnormal ones.

All test results of the healthy subjects tested in a special epidemiologic study were analyzed by separate gender and age groups. For example, all test results of all males of age 30 were put in one group. Predicted values for each HRV parameter were calculated as described above. Then all parameter values (in this example—mean heart rate) were grouped around the predicted values. 5% of the values most deviating from the predicted value are considered as outlying (outside of the normal range). The rest 95% of all values define the normal range.

The ECG recorder considers 15% of the most deviating values among those falling into 95% range as borderline range. Only remaining 80% of all values forms a true normal range used to form an interpretive Autonomic Balance diagram described below. For the subject described in this example a lower borderline level of HF parameter is 2.64. Thus the value shown in the example above falls into a borderline zone.

When using the ECG recorder in FIG. 1 to monitor the dynamics of changes in the autonomic regulatory function or to evaluate the effects of specific factors on this function an important question is usually asked—if the changes in a measured parameter are considered significant or are result of normal variation of the random process. This question is answered based on assessment of the reproducibility and repeatability of the measured parameter. Reproducibility is a variance of a parameter being repeatedly measured in the same subject within a limited time frame. Repeatability reflects natural variance of a specific parameter in the same subject observed during a long period of time (several weeks).

HRV parameters significantly depend on current condition of the subject at a time of testing. Thus it is virtually impossible to obtain absolutely identical readings measured at different moments. This means that the reproducibility and repeatability of the test cannot be 100%. High level of reproducibility and repeatability means only qualitative similarity of any two test results obtained from the same individual at substantially similar conditions of both subject and testing environment. When comparing test results, keep in mind that the autonomic nervous system is fairly sensitive to many internal and external factors including various genetically predetermined and transitory factors, health assessment metrics.

The most appropriate way to assess the autonomic nervous system function is to use so-called predicted values defining normal values of specific HRV parameters, which we expect to obtain from a tested individual if we assume that this individual is healthy. Predicted value is a statistically most probable value of the parameter predicted based on correlation between this parameter values, age and gender of healthy individuals. Predicted values are calculated by the formulae created based on a special study obtained readings from a large population of healthy subjects of different ages and gender.

It's well established that baroreceptor strength declines with age. The reason is that the sensitiveness of the body to any external or internal stimulant makes body easily adaptable to new environment and tells about its strong immunity to fight diseases.

An optimal level of the systemic arterial blood pressure is one of the vital physiological parameters determining adequate function of the cardiovascular system. If arterial pressure is too low then brain, heart and other vital organ do not receive an adequate blood supply so their functions may be affected, e.g. low blood supply to the brain would cause dizziness or even fainting. Alternatively too high arterial pressure causes unnecessary workload to the heart and negatively affects vascular system.

An arterial baroreflex is a key mechanism of short-term regulation of arterial blood pressure. Its whole purpose is to sense minute changes in blood pressure and adjust heart rate to compensate changes in blood supply to the vital organ caused by blood pressure changes. Baroreflex function significantly affects body's ability to adequately react to physical, emotional or mental stressors 93, which may cause significant changes in blood pressure. Decreased baroreflex function may be an early sign of developing cardiovascular disorders such as arterial hypertension and poor overall health 91.

The biological clock 92 test involves continued deep breathing following on-screen instructions for about 1 minute. During that time the ECG recorder analyzes reaction of the user's body on deep paced breathing. The more sensitive the body is, the better shape the user is in. This means that the body is capable to react immediately on changes in internal and external environments, which is a good sign of being younger.

During inhalation the chest is expanding and its internal pressure drops leading to a slight drop in blood pressure because large blood vessels inside the chest are stretched when chest is expanded. The baroreflex causes a quick increase in heart rate as described above. During exhalation the chest contracts so its internal pressure rises causing blood pressure to rise as well due to shrinking large blood vessels in the chest. The baroreflex causes a quick decrease in heart rate as described above. This phenomenon is also known as respiratory sinus arrhythmia. Deep breathing causes maximum possible fluctuations in blood pressure, which helps measuring baroreflex function with larger stimuli. It was found that the highest changes in heart rate induced by deep breathing happen when breathing at the rate of about 6 breaths per minute. Measurement of heart rate oscillations when breathing deeply at 6 breaths per minute is a simple yet effective way to measure baroreflex function. The less sensitive baroreflex is the lesser heart rate oscillations occur.

High baroreflex function is a sign of good vascular elasticity and thus ability of the body to efficiently adapt to various physical, emotional and metal factors causing stress 93 and raise of blood pressure. Low baroreflex function typically is a sign of aging process or certain cardiovascular problem causing stiffness or arterial walls.

The time interval between intrinsic ventricular heart contractions changes in response to the body's metabolic need for a change in heart rate and the amount of blood pumped through the circulatory system. For example, during a period of exercise or other activity, a person's intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform, so that its spectral frequency components can be analyzed and divided into low and high frequency bands. For example, the low frequency (LF) band can correspond to a frequency (LF range 0.04 Hz to <0.15 Hz, and the high frequency (HF) band can correspond to a frequency range (HF range of 0.15 Hz-0.40 Hz). The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as auto-regression) technique from the time domain into the frequency domain. The LF/HF ratio will be used to provide the WM. The LF/HF will be compared to standardized numbers to approximate wellness trends for users.

In another embodiment, the WM may be performed by time domain measurements of the ECG signal. In a continuous ECG record, each QRS complex is detected, and the so-called normal-to-normal (NN) intervals (that is, all intervals between adjacent QRS complexes resulting from sinus node depolarizations) or the instantaneous heart rate is determined. The simplest variable to calculate is the standard deviation of the NN intervals (SDNN), that is, the square root of variance. Since variance is mathematically equal to total power of spectral analysis, SDNN reflects all the cyclic components responsible for variability in the period of recording. The HRV measurement will be used, along with at least one parameter such as body weight, to provide a more complete picture of health.

There needs to be a balance between hard and easy training and rest both within a single training week and within longer training periods. When a hard training session or training period that causes a significant disturbance in body's homeostasis is followed by sufficient recovery, performance improvements are likely to occur. The importance of sufficient recovery is due to the fact that performance improvements actually occur during recovery from training, not during workouts. Finding a balance between training load and recovery is a key factor in improving athletic performance.

Recovery is an important factor with any training regimen. Usually athletes have several very hard training periods each year, during which both the intensity and volume of training are very high. These kind of overreaching periods are very exhaustive but necessary for elite athletes to further improve their performance. However, performance can improve only if hard training is followed by adequate recovery.

Too hard training without sufficient rest may lead to overtraining, which is characterized by decreased performance and in the worst case also other harmful effects on health. Recovery from overtraining may take from several weeks to months, but it is also possible that an athlete never reaches the same level of performance as before overtraining. Prevention of overtraining is therefore crucial, and is possible by systematic assessment of the athlete's recovery. Recovery is defined as decreased activation in the body during relaxation, rest and/or peaceful working, related to lack of external and internal stress factors when parasympathetic (vagal) activity is great and sympathetic activity is low. Recovery is detected when HR is close to the resting level and HRV is great and regular according to the breathing rhythm. Level of HRV is individual. This must be taken into account when interpreting the measured data since analysis is based on HRV. It is recommended that reference values are measured for both high training load/poor recovery and for low training load/well recovered conditions. These reference values should be updated whenever needed, for example between different training periods if changes appear in ANS function.

Respiration can be an indicator of activity, and can provide an explanation of increased sympathetic tone. For example, it may not be appropriate to change or modify a treatment for modulating autonomic tone due to a detected increase in sympathetic activity attributable to exercise. Respiration measurements can be used to measure Respiratory Sinus Arrhythmia (RSA). RSA is the natural cycle of arrhythmia that occurs through the influence of breathing on the flow of sympathetic and vagus impulses to the sinoatrial node (parasympathetic nervous system—PNS). The rhythm of the heart is primarily under the control of the vagus nerve, which inhibits heart rate and the force of contraction. The vagus nerve activity is impeded and heart rate begins to increase when a breath is inhaled. When exhaled, vagus nerve activity increases and the heart rate begins to decrease. The degree of fluctuation in heart rate is also controlled significantly by regular impulses from the baroreceptors (pressure sensors) in the aorta and carotid arteries. Thus, a measurement of autonomic balance can be provided by correlating heart rate to the respiration cycle. The bigger the RSA, the better it is for heart function and blood pressure. Short and rapid breathing is associated with small RSA, and slow and long breath with larger RSA. Thus, slow and long breath is helpful in supporting heart function and lowering blood pressure.

Instant bio-feedback can be provided to the patient, without the need for any interruption arising from repositioning of the device. The bio-feedback derived from HRV and RSA can be used in the areas of stress reduction, rehabilitation, performance enhancement, Migraines and other headaches, AIDS, Depression or Bipolar Disease, Anxiety, Post-traumatic Stress Syndrome, Attention Deficit Disorder, Fibromyalgia, Hypertension, Post-MI, Angina, Atherosclerosis, Mitral Valve Prolapse Syndrome, Cardiomyopathy, Cardiac Dysrhythmias, Congestive Heart Failure, Acquired Hypothyroidism, Thyroid Disorders, Premature Menopausal Symptoms, Menopausal Syndromes, Sleep Apnea, Asthma and COPD (this list is not meant to be exhaustive).

The cover 33 may comprise of memory to store signals for delayed transmission. Conveniently, an archive memory may be used to store standard bio-data such as standard ECG trace of the user, acquired when the user is healthy. This archived bio-signal may then be sent to distant medical professions, along with contemporary signals, when the user/patient is having a crisis. The cover 33 may be coupled to the cell phone by an internal or external connector which extends from the circuitry of the cover to the microphone or data port of the cell phone to transfer the bio-signal data to the cell phone. Data may be transferred to mobile phone or client device using wired or wireless communication 11 comprising at least one of Bluetooth, Zigbee, WiFi, WiMax, IR, a cellular protocol, amplitude modulation or frequency modulation such as Bluetooth, ANT, zigbee and radio. The client device 10 can be a Personal Digital Assistant (PDA), mobile phone, a telehealth hub, laptop computer, personal computer and server. The cover 33 may be powered by its own internal battery source 15 or may piggyback on the power supply of the mobile device. In another embodiment, the power supply 15 is a rechargeable power supply, and more particularly, a rechargeable battery power supply.

In addition to HRV and RSA the ECG recorder can include and/or connected to other sensors and devices that include blood glucose meter, a pacemaker, a blood pressure monitor, an insulin pump, a pulse oximeter, a holter monitor, an electrocardiograph, an electroencephalograph, a blood alcohol monitor, an alcohol breathalyzer, an alcohol ignition interlock, a respiration monitor, an accelerometer, a skin galvanometer, a thermometer, a patient geo-location device, a scale, an intravenous flow regulator, patient height measuring device, a biochip assay device, a sphygmomanometer, a hazardous chemical agent monitor; an ionizing radiation sensor; a monitor for biological agents, a loop recorder, a spirometer, an event monitor, a prothrombin time (PT) monitor, an international normalized ratio (INR) monitor, a tremor sensor, a defibrillator, or any other medical device.

An application programming interface (API) may be used to access data of many different types. In one implementation, the API may be used for bi-directional communication between the wellness cover device and other medical devices for updating and deleting data and metadata.

Beyond a cover, the ECG recorder in FIG. 1 may also be incorporated into a harness, patch/band aid or glove, communicating with mobile or cell phone or client devices, in order to convey the bio-signal into the telephonic transmission portion of the combined device.

In another embodiment, FIG. 10 shows the ECG recorder in the form of a patch. The patch has a soft breathable cover 101. Underneath the breathable cover 101 is a waterproof electronics housing 102, which houses the electronics 104, battery 103 on a flexible circuit board 108. The patch has a flexible backing 110. Electrical leads 107 are attached onto dry ECG sensors 106, running along the breathable, flexible backing 110, which contains adhesive that adheres to the user.

The present invention has now been described with reference to exemplifying embodiments. However, the invention is not limited to the embodiments described herein. On the contrary, the full extent of the invention is only determined by the scope of the appended claims.

What is claimed is:

1. A method of determining health and wellness metrics comprising:
   a. Acquiring an electrical footprint of the heart by a recorder device wherein the recorder device contains at least two dry electrodes, a microprocessor and wireless communication;
   b. Wirelessly transmitting, by the recorder device, the electrical footprint of the heart to a mobile device;
   c. The mobile device transmitting the electrical footprint of the heart to a remote server, wherein the remote server analyzes said electrical footprint of the heart;
   d. Determining and generating health assessment metrics from the electrical footprint of the heart, wherein the health assessment metrics further include overall health, aging and fitness, wherein fitness is assessed from the electrical footprint of the heart and a user's blood pressure drops due to gravitational redistribution of blood mass and aging is assessed from the electrical footprint of the heart and the user's baroreflex analysis, causing fluctuations in blood pressure;
   e. Generating stress, relaxation and an idle states, wherein each of the states has three different levels of autonomic tonus;
   f. Transmitting the health assessment metrics and the nine stress, relaxation and idle states to the mobile device and archiving the said the health assessment metrics and stress, relaxation and idle states after transmission;
   g. Displaying on the mobile device the health assessment metrics, and the stress, relaxation and idle states, wherein each of the states has three different levels of the autonomic tonus.

2. The method according to claim 1, wherein the wireless transmission is Bluetooth.

3. The method according to claim 1, wherein the health assessment metrics further include overall health, aging and fitness.

4. The method according to claim 1, wherein the mobile device is a cellular telephone.

5. The method according to claim 1, wherein the mobile device is a tablet computer.

6. The method according to claim 1, wherein electrical footprint of the heart is electrocardiogram (ECG).

7. The method according to claim 6, wherein the acquisition of the ECG is from a chest patch with at least two dry ECG sensors, with backing that contains adhesive that adheres to a user.

8. A system for determining health and wellness metrics comprising:
  a. A heart electrical footprint recorder device with biological sensors, wherein said recorder device contains at least two dry electrodes, non-transitory computer readable medium, a microprocessor and software being executed to:
    i. Acquire at least the heart electrical footprint signal;
    ii. Transmit the at least heart electrical footprint signal to a client device;
  b. A client device wherein said client device contains non-transitory computer readable medium, a processor and software being executed to:
    i. Display at least the heart electrical footprint signal;
    ii. Record and review the heart electrical footprint signal;
    iii. Generate health assessment metrics from the electrical footprint of the heart, wherein the health assessment metrics further include overall health, aging and fitness, wherein fitness is assessed from the electrical footprint of the heart and a user's blood pressure drops due to gravitational redistribution of blood mass and aging is assessed from the electrical footprint of the heart and the user's baroreflex analysis, causing fluctuations in blood pressure;
    iv. Generate stress, relaxation and an idle states wherein each of the states has three different levels of autonomic tonus;
    v. Transmit the at least heart electrical footprint signals to a remote server;
    vi. Display the health assessment metrics, and the stress, relaxation and idle states, wherein each of the states has three different levels of the autonomic tonus;
  c. A remote server wherein said remote server contains non-transitory computer readable medium, a processor and software being executed to:
    i. Analyze at least heart electrical footprint and determine the health assessment metrics, and the stress, relaxation and idle states;
    ii. Transmit and archive the health assessment metrics and stress, relaxation and idle states to the client device.

9. The system according to claim 8, wherein the transmission of the electrical footprint of the heart to the client device is wireless.

10. The system according to claim 9, wherein the wireless transmission is Bluetooth.

11. The system according to claim 9, wherein the wireless transmission is Wi-Fi.

12. The system according to claim 8, wherein the transmission is wired.

13. The system according to claim 8, wherein client device is a mobile phone.

14. The system according to claim 8, wherein the client device is laptop computer.

15. The system according to claim 8, wherein the client device is personal computer.

16. The system according to claim 8, wherein the client device is tablet computer.

17. The system according to claim 8, wherein the health assessment metrics further include overall health, aging and fitness.

18. The system according to claim 8, wherein the acquisition of the ECG is from a chest patch with at least two dry ECG sensors, with backing that contains adhesive that adheres to a user.

19. A system for determining health and wellness metrics comprising:
  a. A Processor;
  b. Non-transitory computer-readable medium with instructions stored therein and being executed to perform the following:
    i. Acquiring an electrical footprint of the heart;
    ii. Wirelessly transmitting the electrical footprint of the heart to a mobile device;
    iii. transmitting the electrical footprint of the heart to a remote server, wherein the remote server analyzes said electrical footprint of the heart;
    iii. Determining and generating health assessment metrics from the electrical footprint of the heart from the electrical footprint of the heart, wherein the health assessment metrics further include overall health, aging and fitness, wherein fitness is assessed from the electrical footprint of the heart and a user's blood pressure drops due to gravitational redistribution of blood mass and aging is assessed from the electrical footprint of the heart and the user's baroreflex analysis, causing fluctuations in blood pressure;
    iv. Generating stress, relaxation and an idle states, wherein each of the states has three different levels of autonomic tonus;
    v. Transmitting the health assessment metrics and the nine stress, relaxation and idle states to the mobile device and archiving the said the health assessment metrics and stress, relaxation and idle states after transmission;
    vi. Displaying on the mobile device the health assessment metrics, and the stress, relaxation and idle states, wherein each of the states has three different levels of the autonomic tonus.

* * * * *